United States Patent [19]

Barstow et al.

[11] Patent Number: 5,001,224

[45] Date of Patent: Mar. 19, 1991

[54] ORGANIC SYNTHESES EMPLOYING SUPERCRITICAL CARBON DIOXIDE AS A REACTION SOLVENT

[75] Inventors: Leon E. Barstow; Glen D. Ward; Milan Bier, all of Tucson, Ariz.

[73] Assignee: Protein Technologies, Inc., Tucson, Ariz.

[21] Appl. No.: 167,201

[22] Filed: Mar. 11, 1988

[51] Int. Cl.$^5$ ............................ C07K 1/02; C07K 1/04
[52] U.S. Cl. ..................................... 530/334; 530/333; 530/338; 564/132
[58] Field of Search ....................... 530/334, 333, 338; 564/132

[56] References Cited

U.S. PATENT DOCUMENTS 4,483,996 11/1984 Jacobson ............................. 549/524
4,820,752 4/1989 Berens et al. ....................... 523/340

OTHER PUBLICATIONS

Hyatt, John A., J. Org. Chem. 49; 5097–5101, 1984.
Sigman, Michael E., J. Org. Chem., 52; 1754–1757, 1987.
Futuretech, No. 37, Jul. 13, 1987.
Futurecorp 093–02/11/88.
Kamihira, Chemical Abstracts, 109(9): 73891 v, Published 1987.

Primary Examiner—Howard E. Schain
Assistant Examiner—Susan M. Perkins
Attorney, Agent, or Firm—Kenyon & Kenyon

[57] ABSTRACT

Chemical reactions are readily carried out using supercritical carbon dioxide as the reaction medium. Supercritical carbon dioxide is of special value as a reaction medium in reactions for synthesizing polypeptides, for sequencing polypeptides, or for amino acid analysis.

3 Claims, No Drawings

ORGANIC SYNTHESES EMPLOYING SUPERCRITICAL CARBON DIOXIDE AS A REACTION SOLVENT

This invention was made with Government support under SBIR Contract No. NAS 2-12563 awarded by the National Aeronautics and Space Administration (NASA). The Government has certain rights in this invention.

This invention pertains to a new procedure for conducting chemical reactions in a less expensive manner that in many cases may yield a reaction product in a purer form than heretofore possible. It has particular applicability to processes for forming synthetic polypeptides and amino acid derivatives by reactions at carbon and nitrogen to form esters and amides.

BACKGROUND OF THE INVENTION

It is well known that for many chemical reactions to occur at practical rates at least one of the reactants must be dissolved in an inert solvent. For many organic reactions, those solvents are liquid hydrocarbons or halogenated hydrocarbons, such as chloroform, methylene chloride and chloromethane.

In many cases, the use of such solvents give satisfactory yield of product but presents problems and expense in solvent costs, manipulation, recovery and disposal. There are certain reactions important to biochemistry, such as polypeptide syntheses, in which such solvents pose certain problems. Polypeptides are frequently prepared by sequential addition of protected amino acids to a growing peptide chain attached to a solid substrate, such as a polystyrene or porous glass substrate. As presently practiced, these reactions do not go 100% to completion.

For example, conventional techniques using solid supports sometimes suffer from incomplete reaction because of the solvent's inability to penetrate the resin. As a consequence, the final product often is a complex mixture of polypeptides which is difficult to purify. The synthesis is further complicated by the presence of organic reaction solvents which also must be removed. Moreover, such solvents tend to be fairly expensive and can materially increase the cost to manufacture certain products.

It would be highly desirable to have a low cost solvent which is readily removed from the reaction products, which can easily dissolve reagents, and which has high penetrating power, and thus is more easily able to penetrate porous solid reaction substrates or solid reactants.

DESCRIPTION OF THE INVENTION

The present invention is based upon the discovery that supercritical carbon dioxide is a very economical, and highly flexible reaction solvent for organic reactions.

As is well known, all gases have a critical temperature and pressure—the critical temperature being the temperature above which the gas cannot be liquified by increasing pressure, and the critical pressure being the pressure necessary to liquify the gas at the critical temperature. For carbon dioxide, the critical temperature is 88° F. (31.1° C.) and the critical pressure is 1073 psi. The term "supercritical carbon dioxide", as used herein, refers to carbon dioxide at a temperature greater than 88° F. and a pressure greater than 1073 psi.

Carbon dioxide in its supercritical state has a number of properties making it a very desirable reaction solvent. It is inert under a wide variety of organic reaction conditions. It has a high diffusivity and is readily able to penetrate solid phase supports. Since it is inexpensive and non-toxic, it can be vented to the atmosphere for disposal. It is easily used where anhydrous conditions must be maintained. It minimizes problems in recovery of reaction product because the solvent is removed simply by reducing pressure to subcritical, thereby avoiding the need for repeated washings to remove spent reagents, side products and other reaction solvents.

Supercritical carbon dioxide may be used in any chemical reaction in which a chemical reaction product is obtained by contacting two or more reactive chemical moieties in the presence of an inert reaction solvent, causing combination of the moieties to form the reaction product, under the conditions needed to maintain supercritical carbon dioxide. The moieties may be the same or different. The moieties each may have a single reactive site, or they may have more than one. The reaction may be a conventional reaction to form a low molecular weight chemical, such as an ester, an ether, an amide, etc., or it may be a dimerization, trimerization, oligomerization or polymerization.

Supercritical carbon dioxide may be the sole solvent, but other solvents may be present and still achieve the benefits attributable to supercritical carbon dioxide. Thus, if reactants are obtained in the form of solutions, the solution may be used without first separating the reactant from the solvent.

The reactions may be carried out at any temperature above the critical temperature of carbon dioxide, and any pressure above its critical pressure, consistent with the stability of reactants and reaction products, and with the desired rates of the desired reaction and undesired side reactions with carbon dioxide. It has been found that many reactions readily occur at temperatures from about 90° F. to about 150° F., and at pressures from about 1073 psi up to 4000 psi or even higher.

The use of supercritical carbon dioxide is of special importance in carrying out reactions used in peptide synthesis, such as acylation, e.g., acetylation, of primary and secondary amines with various acylating reagents such as acylimidazoles, e.g., acetylimidazole, acyl chlorides, e.g., acetylchloride, or acyl anhydrides, e.g. acetic anhydride and esterification of alcohols with reagents such as acylimidazoles, acyl anhydrides and acyl chlorides.

For example, a common solid-phase process for the synthesis of synthetic polypeptides, known as the Merrifield method, starts with an amino acid coupled to a solid support, commonly a polystyrene resin, through the carboxyl group of the amino acid. In addition, the α-amino group is protected against undesired reactions by a t-butoxycarbonyl (BOC) protecting group. The conventional polypeptide synthesis proceeds by removing the BOC protecting group (deprotection) by treatment with a mild acid such as trifluoroacetic acid (TFA) in dichloromethane, washing with dichloromethane to remove all traces of TFA, neutralizing with triethylamine (TEA) in dichloromethane, washing with dichloromethane to remove excess TEA and its salts, reacting the deprotected resin-amino acid with a BOC-protected amino acid dissolved in dichloromethane in the presence of a carboxyl activating agent such as dicyclohexyl carbodiimide (DCC), washing with dichloromethane to remove soluble reagents and by-products, washing with methanol to remove dicyclohexyl urea by-product which is insoluble in dichloromethane, and washing with dichloromethane to remove methanol. The sequence may be represented as follows:

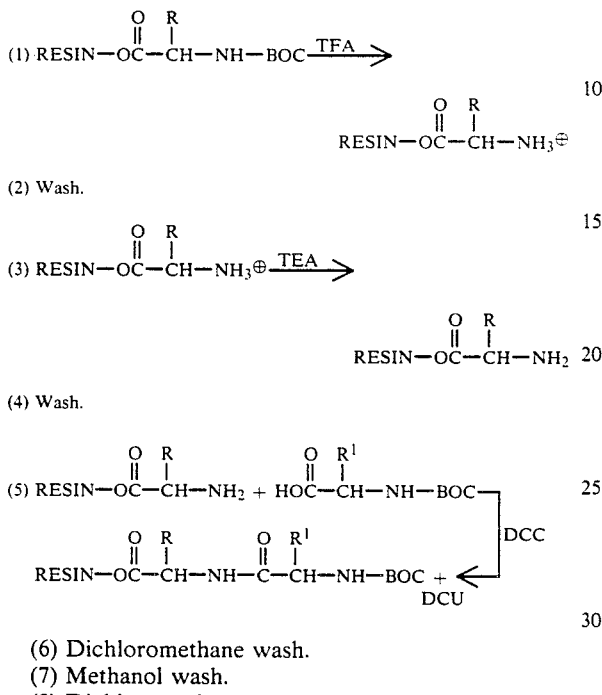

(6) Dichloromethane wash.
(7) Methanol wash.
(8) Dichloromethane wash.

Since most wash steps are performed two or three times each, the procedure is very time consuming, with a complete cycle requiring up to two hours for each amino acid incorporated into the peptide chain. This procedure has several drawbacks, including the extensive use of chlorinated solvents, frequent incomplete couplings, reduced yields due to trifluoroacetylation of the amino group during repetitive deprotection steps, reactions with the side chain of the amino acid, and premature cleavage of the peptide chain from the support. As a consequence, the final product is inhomogeneous, and may even contain peptides which have activity antagonistic to the activity of the desired peptide hormone.

An alternate solid phase synthesis employs the base liable fluorenylmethoxycarbonyl (FMOC) protecting group on the α-amino group. This group is removed by piperidine (Pip) or other organic base dissolved in dimethylforamide (DMF), the resin is washed with DMF to remove excess and spent FMOC reagents, piperidine and its salts, the deprotected resin is reacted with an activated FMOC-protected amino acid, such as pentafluorophenyl ester of the acid, and the resin is washed with DMF to remove by-products and excess ester. This sequence may be illustrated as follows:

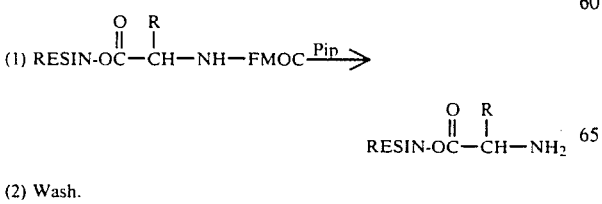

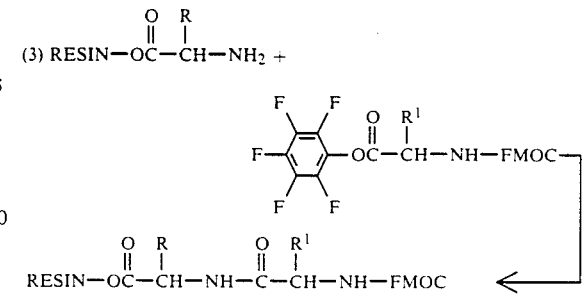

(4) Wash.

While this scheme has fewer steps than the BOC scheme, it still has numerous washings and suffers from some of the same problems with respect to yield and formation of an inhomogeneous product.

Prior to the development of solid phase techniques, peptides had been synthesized in solution by reacting an amino acid with a reactive amino acid derivative such as the N-carboxylanhydride (NCA) followed by removal of carbon dioxide, as follows:

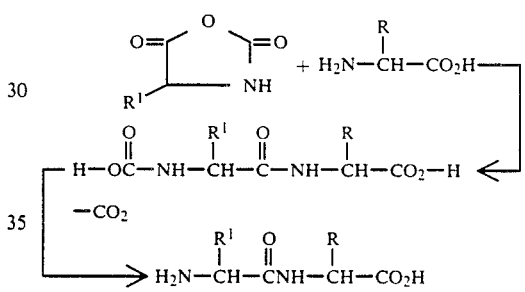

While this procedure is quite simple because the amino acid NCA reacts directly with the free α-amino group without activation, and the product is a peptide carbamate which acts as a protecting group, it has not been widely used because of low yields and it usually gives an impure product. The carbamate group is unstable in solutions below pH of 11, and decarboxylation occurs leaving free amino groups which cause polymerization or over-reaction. If the pH is increased above 11, other competing reactions occur as a result of hydrolyses or the formation of hydantoic acid. As a consequence, coupling efficiencies normally do not exceed 90-95%, and the practical value of this technique is limited to large-scale production of small peptides.

Supercritical carbon dioxide can be used as a reaction solvent for processes for polymerizing N-carboxylanhydride or its derivatives to form peptide homopolymer and copolymers having repeating α-amino acid units.

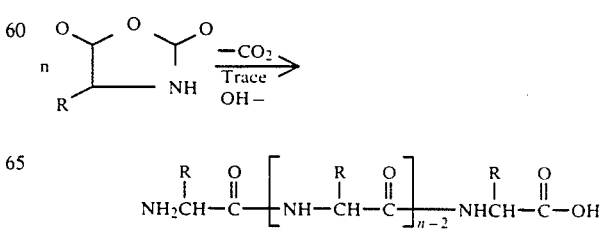

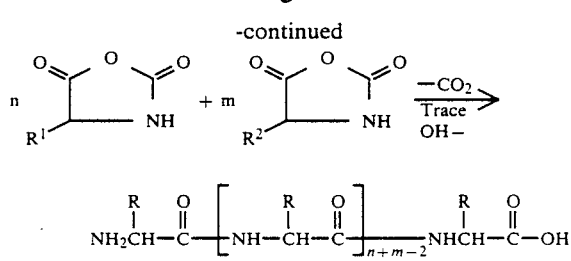

$$NH_2CH\underset{R}{-}\underset{\|}{\overset{O}{C}}-\left[-NH-\underset{R}{\overset{|}{C}}H-\underset{\|}{\overset{O}{C}}-\right]_{n+m-2}NHCH\underset{R}{-}\underset{\|}{\overset{O}{C}}-OH$$

In the second reaction, the "R" side-chain will vary depending upon $R^1$ or $R^2$ and the relative proportions of co-monomers. Terpolyamides and higher polymers can be obtained through use of three or more starting anhydride monomers.

In the above-mentioned reaction schemes, R and $R^1$ represent hydrogen or α-amino acid side chains, such as hydrocarbon side chains of α-amino acids such as alanine, valine, leucine, isoleucine, and phenylalanine, and substituted hydrocarbon side chains of amino acids such as tyrosine, threonine, serine, tryptophane, thyroxine, methionine, cysteine, lysine, arginine, histidine, aspartic acid, and glutamic acid. In addition, α-amino acids in which the side chain combines with the α-amino group to form a heterocyclic ring, such as proline and hydroxyproline, may be employed. This invention is not, of course, limited to the naturally-occurring amino acids, or to the specific syntheses specified herein. On the contrary, it can be employed advantageously in any procedure for producing a peptide oligomer or polymer.

Use of supercritical carbon dioxide as a solvent is of immense value in the preparation of peptides. It may be used in solid phase syntheses, and is of particular value where the support is a controlled pore glass (CPG) bed. The high diffusibility of supercritical carbon dioxide assures penetration of the pores of the substrate. Further, volatile reagents may be removed simply by venting the compressed fluid, yielding a dry powder, thereby avoiding the need to dispose of or recycle organic solvents. The time and expense saved can be enormous when synthesizing polypeptides with, e.g., 20 to 40 amino acids, such as calcitonin. Anyhdrous conditions are required for some reactions to give a 100% coupling yield, and such reactions are readily carried out with supercritical carbon dioxide. Use of carbon dioxide also reduces the cost of the procedure because it is considerably cheaper than the chlorinated hydrocarbons normally used as solvents, and because it is non-toxic, it can be vented to the atmosphere. Moreover, by avoiding the need for large volumes of liquid solvents, use of supercritical carbon dioxide can permit the construction of low cost commercial scale production equipment for the manufacture of polypeptides that is only slightly larger than laboratory-size equipment.

The use of supercritical carbon dioxide as a reaction solvent is also of benefit for the liquid phase synthesis using amino carboxyl anhydrides (NCA) as reagents, in that it may stabilize the carbamate protecting group and facilitate the separation of the reaction products from solvents before the next chemical reaction.

Supercritical carbon dioxide may also be useful as a reaction solvent in the analysis of amino acid from proteins. In conventional amino acid analyses, a protein is hydrolyzed to its individual amino acid components, and the amino acids are separated, identified and quantitated. Detection of the amino acids depends on producing a derivative that can be measured by ultra-violet absorption, color or fluorescence. The first automated method for amino acid analysis, which was introduced by Moore and Stein in 1951, uses ion exchange columns to separate the amino acids. A colored derivative is made of each amino acid by the reaction of ninhydrin with the alpha-amino group of the amino acid. These colored compounds are then detected using a colorimeter and, when compared with standard concentrations and retention times, give both a qualitative and quantitative analysis. The Moore and Stein technique is the primary example of a post-column derivatization method for amino acid analysis.

Recently, several pre-column methods have been developed, in which derivatives of the amino acids are prepared in the crude hydrolyzed mixture. The resulting mixture of amino acids is then separated by reverse phase HPLC chromatography and the amino acids are identified qualitatively by retention time and quantitatively by comparison of the color adsorption with a standard. There are several reagents that have been used for preparing derivatives in the pre-column methods, including phenylisothiocyanate, orthophthalaldyde and dansyl chloride.

Use of supercritical carbon dioxide as the solvent for these reactions is of great importance because many proteins of biological interest are normally found in very minute quantities. It is important, therefore, to have very sensitive quantitative analytical procedures.

Supercritical carbon dioxide is also of value in protein sequencing techniques for determining the primary structure of proteins. In the basic sequencing technique, known as the Edman Degradation [Cf. Edman, P., Acta. Chem. Scand. Iv. 283 (1950)], phenylisothiocyanate is used to make a derivative of the N-terminal alpha-amino acid. This derivative, when treated with an anhydrous organic acid such as trifluoroacetic acid, cyclizes to remove the N-terminal amino acid and produce an anilinothiazolone amino acid derivative. This somewhat unstable derivative is then converted on treatment with strong acid to phenylthiohydantoin. The reaction sequence may be illustrated as follows:

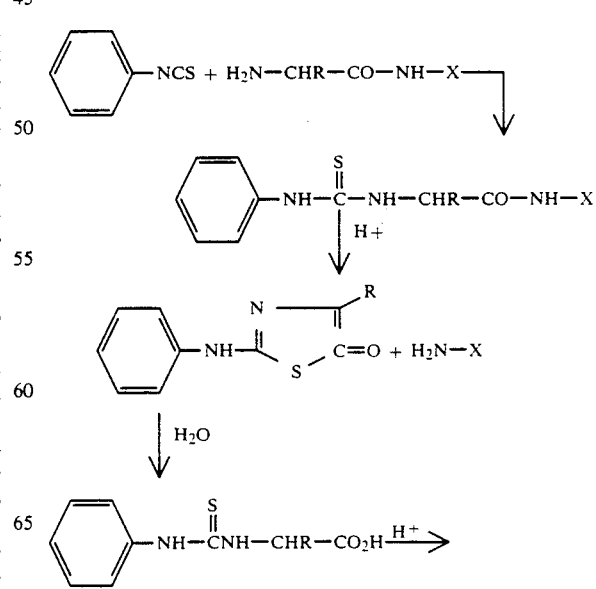

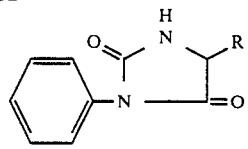

The phenylthiohydantoin amino acid (PTC amino acid) is identified by chromatography and quantified using a comparison of its fluorescence adsorption with a standard. The Edman technique can be done manually, however, it is a tedious job requiring highly skilled technicians.

A number of groups have developed automated Edman techniques including the liquid phase spinning cup sequencer covered by U.S. Pat. No. 3,725,010, the solid phase/liquid sequencer developed by Laursen, R. A., Eur. J. Biochem. 20 (1971), and the gas phase sequencer covered by U.S. Pat. No. 4,065,412. The gas phase sequencer has been a significant commercial success because it allows the sequencing of very small amounts of protein.

Use of supercritical carbon dioxide as a substitute for the organic solvents involved in any of the above modifications of the Edman procedure not only improves the chemical yield, but also significantly reduces the mechanical losses due to wash-out by the liquid solvent. In addition to the improved chemistry, the analysis of the resulting derivative is more effective because the carbon dioxide solvent can be removed by routing the supercritical carbon dioxide containing the amino acid derivative through an HPLC injection valve and the carbon dioxide is removed simply by reducing the pressure to sub-critical. The analysis of the derivative is then performed with a standard HPLC reverse phase system. A much more sensitive analysis is obtained by depositing the derivative in the inlet port of a mass spectrometer by reducing the pressure to sub-critical. The combination of improved chemistry, reduced mechanical yields and improved delivery to the analytical system very significantly increases the sensitivity and allows the determination of the secondary structure of proteins on sub-picomole quantities.

The phenylisothiocyanate reaction described above takes place with the α-amino group of the protein at moderate pH (e.g., 7–9); however, at higher pH the reaction also takes place on the basic side chains of amino acids like lysine, ornathine and arginine.

The use of supercritical carbon dioxide as a reaction solvent is also beneficial in the analysis of individual α-amino acids, such as a mixture of α-amino acids obtained by hydrolysis of a protein or a polypeptide. In such analyses, a derivatizing agent is added to the amino acid or mixture of amino acids, and allowed to react to form a derivative. Suitable derivatizing agents include phenylisothiocyanate, dansyl chloride, orthophthaldehyde, ninhydrin, dinitrobenzene and fluorescamine. These protein derivatives may be made in supercritical carbon dioxide to increase the sensitivity of the analysis by improving the yield of the chemical reaction, decreasing the amount of side reaction(s) and improving the delivery to the analytical system.

Amino acids must be derivatized to make them chromagenic or fluorogenic before they can be detected on minute quantities by standard analytical spectrometers. The same derivatives described for protein analysis above are useful for amino acid analysis and may be made in supercritical carbon dioxide. This approach may give much improved sensitivity over current solution methods.

The following examples are illustrative. All reactions were carried out in a Super Critical Fluid System made by Milton Roy, of Ivyland, Penna., employing as a reaction vessel a 55 ml. pressure vessel rated to 5000 psi, provided with a bottom inlet for compressed $CO_2$ and a top outlet for venting the vessel. As a general rule, liquid reactants were adsorbed on a filter medium while solid reactants were placed in an envelope of folded filter paper. The reactant which was more soluble in supercritical $CO_2$ was placed in the chamber nearer the $CO_2$ inlet, so that it had to be extracted by the $CO_2$ stream before it contacted the less soluble reactant.

EXAMPLE I

A filter medium containing 1 ml. of liquid n-butanol was placed in the vessel adjacent the $CO_2$ inlet, and 550 mg. solid acetylimidazole was placed above the filter medium. The system was then charged with carbon dioxide at 96° F. and 3000 psi and allowed to react for one hour. The system was reduced to subcritical conditions and vented to the atmosphere. The liquid reaction product was drained out of the reaction vessel and was found by gas chromatography and mass spectroscopy to be butyl acetate in 57% yield.

EXAMPLE II

Using similar procedures, 660 mg. of solid acetylimidazole was reacted with 516 mg. of liquid 5-amino-1-pentanol. The system was charged with carbon dioxide at 3000 psi and 154° F. and allowed to react for 4 hours. The system was vented and disassembled, and the filter media were soaked in 5 ml. chloroform for about 5 minutes to extract reaction products. The chloroform solution was analyzed by gas chromatography and mass spectroscopy and found to contain, in addition to the two starting materials, N,O-diacetyl-5-aminopentanol, N-acetyl-5-amino-1-pentanol and O-acetyl-5-amino-1-pentanol.

EXAMPLE III

Using procedures similar to those described in Example I, 1 ml. of liquid acetic acid anhydride was reacted with 150 mg. of BOC-Valine Merrifield resin which had been deprotected by removal of the t-butoxycarbonyl protecting group by the method of Coenen, et al., German Chemical Engineering, 7, 335 (1984). The vessel was charged with carbon dioxide at 3000 psi and 94° F. and allowed to react for 20 minutes. The system was reduced to subcritical conditions and vented to the atmosphere. Acetylation of the deprotected valine residue was greater than 99.4% complete by ninhydrin analysis using the Kaiser procedure described in McHugh, et al., Supercritical Fluid Extraction, Butteworth & Co., Ltd. (1986).

EXAMPLE IV

Using procedures similar to those described in Example I, 100 mg. of commercially-available long chain alkyl amine controlled pore glass (LCAA-CPG) resin was reacted with 200 mg. of solid acetylimidazole. Both reactants were placed in filter paper envelopes, with the envelope containing acetylimidazole being placed in the vessel below the envelope containing the LCAA-CPG. The system was charged with carbon dioxide at 3000 psi and 95° F., and the reaction was allowed to proceed for one hour. The vessel was then reduced to subcritical conditions and vented to the atmosphere. Analysis of a small sample of the resin with the Kaiser ninhydrin reagent showed that acetylation of the LCAA-CPG resin was complete.

EXAMPLE V

Employing procedures similar to those described in Examples I, III and IV, 200 mg. of BOC-Valine Merrifield resin was deprotected and the deprotected resin was reacted with 220 mg. of solid acetylimidazole for 2 hours in the presence of carbon dioxide at 100° F. and 3000 psi. Analysis of small samples of the resin with the Kaiser ninhydrin test showed acetylation was less than 74% complete. Based upon the results of Examples III–V, it appears that LCAA-CPG resin is a better support when a solid acylating agent is employed, while both the LCAA-CPG resin and the polystyrene-based Merrifield resin can be employed when a liquid acylating agent is employed.

EXAMPLE VI

Using procedures similar to those described in Example IV, 100 mg. of LCAA-CPG resin was reacted with 272 mg. of solid N-hydroxysuccinimide ester of BOC-glycine for 5 hours in carbon dioxide at 3000 psi and 96° F. It was found that 240 mg. of the BOC-glycine ester remained in the envelope, indicating that only 32 mg. had dissolved in the carbon dioxide. Analysis of a small sample of the resin with Kaiser ninhydrin indicated that reaction of the protected glycine with the LCAA-CPG resin was about 94% complete.

EXAMPLE VII

Employing procedures similar to those described in Example IV, a solution containing 1.0 mM of the symmetric anhydride of BOC-glycine was reacted with 100 mg. of LCAA-CPG for 105 minutes in carbon dioxide at 3500 psi and 100° F. Analysis of a small sample of the resin with Kaiser ninhydrin reagent demonstrated that coupling of BOC-glycine with the LCAA-CPG was complete.

EXAMPLE VIII

Employing procedures similar to those described in Example IV, 87 mg. of a Gly-LCAA-CPG resin made by deprotecting the product of Example VII by standard techniques, was reacted with 552 mg. of the BOC-leucine p-nitrophenyl ester for about 16 hours (overnight) in carbon dioxide at 3100 psi and 101° F. Analysis of a small sample of the resin product with Kaiser ninhydrin reagent demonstrated that the coupling with BOC-leucine was complete to form a BOC-Leu-Gly-LCAA-CPG resin.

EXAMPLE IX

Employing procedures similar to those described in Example VIII, the product of Example VIII was deprotected and reacted with 0.5 mM of the symmetric anhydride of BOC-glycine for 90 minutes in carbon dioxide at 3000 psi and 105° F. Analysis of a small sample of the resin showed that coupling of the BOC-glycine to produce a BOC-Gly-Leu-Gly-LCAA-CPG resin was complete.

EXAMPLE X

Using procedures similar to those described in Example VIII, the product of Example IX was deprotected and the deprotected product was reacted with 0.5 mM of the symmetric anhydride of BOC-alanine for 90 minutes in carbon dioxide at 3000 psi and 105° F. Analysis of a small sample of the resin showed that coupling of the BOC-alanine to produce BOC-Ala-Gly-Leu-LCAA-CPG resin was complete.

The thus-produced resin was hydrolyzed with 0.5 ml. concentrated hydrochloric acid/propionic acid (1:1, V/V) overnight at 110° C. The resulting mixture was evaporated to dryness and the solid resin was mixed with 1 ml. water. The resulting aqueous solution was drawn into a syringe fitted with a 0.22 um filter, the water was evaporated and the tube was sealed for amino acid analysis by standard procedures on a Beckman 890 amino acid analyzer. Only glycine, alanine and leucine were found present in a molar ratio of 2:1:1.

EXAMPLE XI

Using procedures similar to those described in Example IV, 250 mg. of an LCAA-CPG resin to which 4-hydroxymethylbenzoic acid had been attached as a base-labile link, using standard symmetric coupling techniques, was reacted with 0.25 mM of the symmetric anhydride of BOC-valine for 1 hour in carbon dioxide at 2800 psi and 103° F. Analysis of a small portion of the resin by the Kaiser ninhydrin reagent demonstrated the coupling reaction to form BOC-Val-HMBA-LCAA-CPG resin was complete.

EXAMPLE XII

Using procedures similar to those described in Example IV, all of the product of Example XI was deprotected and reacted with 0.25 mM of the symmetric anhydride of BOC-glycine for 1 hour in carbon dioxide at 2800 psi and 103° F. Analysis of a small portion of the resin by the Kaiser ninhydrin reagent demonstrated the coupling reaction to form BOC-Gly-Val-HMBA-LCAA-CPG resin was complete.

EXAMPLE XIII

Using procedures similar to those described in Example IV, all of the product of Example XII was deprotected and reacted with 0.25 mM of the symmetric anhydride of BOC-alanine for 1 hour in carbon dioxide at 2800 psi and 103° F. Analysis of a small portion of the resin by the Kaiser ninhydrin reagent demonstrated the coupling reaction to form BOC-Ala-Gly-Val-HMBA-LCAA-CPG resin was complete.

EXAMPLE XIV

Using procedures similar to those described in Example IV, all of the product of Example XII was deprotected and reacted with 0.25 mM of the symmetric anhydride of BOC-leucine for 1 hour in carbon dioxide at 2800 psi and 103° F. Analysis of a small portion of the resin by the Kaiser ninhydrin reagent demonstrated the coupling reaction to form BOC-Leu-Ala-Gly-Val-HMBA-LCAA-CPG resin was complete.

EXAMPLE XV

A 2-3 ml. portion of 40% trifluoroacetic acid in dichloromethane was placed in the vessel and 50 mg. of the product of Example IV, contained in a filter paper envelope was placed in the vessel. The vessel was charged with carbon dioxide at 2800 psi and 120° F., and the reaction was allowed to proceed for 1 hour. After reducing the system to subcritical conditions, venting to the atmosphere, removal of the resin and neutralization, analysis of a small sample of the product with Kaiser ninhydrin reagent showed greater than 95% removal of the BOC protecting group to leave a free amino group.

EXAMPLE XVI

Employing procedures similar to those described in Examples IV, Merrifield's peptide was prepared by reacting, in turn, protected valine, protected glycine, protected alanine and protected leucine with long chain aliphatic amine controlled pore glass beads, using supercritical carbon dioxide at 95° F. and 3000 psi as the reaction solvent.

A 100-mg. sample of this was reacted with 1.0 ml. of a 5% solution of phenylisothiocyanate in hexane for 1 hour in carbon dioxide at 3300 psi and 100° F., to form the phenyl thiocarbanyl. This product was treated with 2.0 ml. anhydrous trifluoroacetic acid, and the resulting trifluoroacetic acid solution was analyzed in a high pressure liquid chromatography system on a standard Beckman 990 Spinning Cup Sequencer. The predominant peak was phenylisothiocyanate leucine hydantoin.

I claim:

1. In a process for producing a chemical reaction product by contacting at least two different reacting moieties in the presence of an inert, substantially anhydrous, reaction solvent, an improvement which comprises using supercritical carbon dioxide as the principal reaction solvent, and wherein an amide linkage is formed by reacting an amine with an acylating agent.

2. A process according to claim 1, wherein said amine is an $\alpha$-amino acid, a protected amino acid, or a peptide chain having at least one $\alpha$-amino group.

3. A process according to claim 2, wherein said acylating agent is a carboxylic acid, a carboxylic acid ester, an N-carboxyl anhydride, an acylimidazole or a symmetrical acyl anhydride.

* * * * *